US00PP20654P2

(12) United States Plant Patent
Michalik

(10) Patent No.: US PP20,654 P2
(45) Date of Patent: Jan. 19, 2010

(54) ***GERANIUM* PLANT NAMED 'REGBURG'**

(50) Latin Name: *Pelargonium grandiflorum*
Varietal Denomination: Regburg

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 363 days.

(21) Appl. No.: 11/820,024

(22) Filed: Jun. 15, 2007

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent L Bell
(74) *Attorney, Agent, or Firm*—C. A. Whealy

(57) ABSTRACT

A new and distinct cultivar of Regal *Geranium* plant named 'Regburg', characterized by its upright and mounded plant habit; vigorous growth habit; freely basal branching habit; early and freely flowering habit; large rich red purple-colored flowers; and no requirement for cooling treatment for flower development.

1 Drawing Sheet

Botanical designation: *Pelargonium grandiflorum.*
Cultivar denomination: 'Regburg'.

BACKGROUND OF THE INVENTION

The present invention relates to a new and distinct cultivar of Regal *Geranium*, botanically known as *Pelargonium grandiflorum*, and hereinafter referred to by the name 'Regburg'.

The new Regal *Geranium* is a product of a planned breeding program conducted by the Inventor in Dresden, Germany. The objective of the breeding program is to develop new Regal *Geraniums* that do not require a cooling treatment for flower development.

The new Regal *Geranium* originated from a cross-pollination made by the Inventor in Dresden, Germany during the summer of 2001 of two unnamed proprietary selections of *Pelargonium grandiflorum*, not patented. The cultivar Regburg was discovered and selected by the Inventor as a flowering plant from within the progeny of the stated cross-pollination in a controlled environment in Dresden, Germany in March, 2002.

Asexual reproduction of the new Regal *Geranium* by vegetative terminal cuttings in a controlled environment in Dresden, Germany since October, 2002, has shown that the unique features of this new Regal *Geranium* are stable and reproduced true to type in successive generations.

SUMMARY OF THE INVENTION

The cultivar Regburg has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Regburg'. These characteristics in combination distinguish 'Regburg' as a new and distinct cultivar of Regal *Geranium:*

1. Upright and mounded plant habit.
2. Vigorous growth habit.
3. Freely basal branching habit.
4. Early and freely flowering habit.
5. Large rich red purple-colored flowers.

6. Does not require cooling treatment for flower development.

Plants of the new Regal *Geranium* differ primarily from plants of the parent selections in flower coloration.

Plants of the new Regal *Geranium* can be compared to plants of the *Pelargonium grandiflorum* cultivar Burghi, not patented. In side-by-side comparisons conducted in Dresden, Germany, plants of the new Regal *Geranium* differed from plants of the cultivar Burghi in the following characteristics:

1. Plants of the new Regal *Geranium* had larger and thicker leaves than plants of the cultivar Burghi.
2. Plants of the new Regal *Geranium* were more freely flowering and flowered earlier than plants of the cultivar Burghi.
3. Plants of the new Regal *Geranium* had smaller flower umbels and smaller flowers than plants of the cultivar Burghi.
4. Plants of the new Regal *Geranium* and the cultivar Burghi differed slightly in flower color.

BRIEF DESCRIPTION OF THE PHOTOGRAPH

The accompanying colored photograph illustrates the overall appearance of the new Regal *Geranium*, showing the colors as true as it is reasonably possible to obtain in colored reproductions of this type. Colors in the photograph may differ slightly from the color values cited in the detailed botanical description which accurately describe the colors of the new Regal *Geranium*. The photograph comprises a side perspective view of a typical flowering plant of 'Regburg' grown in a container.

DETAILED BOTANICAL DESCRIPTION

The aforementioned photograph and following observations, measurements and values describe plants grown in Dresden, Germany in a glass-covered greenhouse during the winter and spring and under conditions which closely approximate commercial *Geranium* production. During the production of the plants, day temperatures averaged 18° C., night temperatures averaged 16° C. and light levels ranged from 15 kilolux to 100 kilolux. Plants were about six months old when the photograph and the description were taken. In the detailed description, color references are made to The Royal Horticultural Society Colour Chart, 1995 Edition, except where general terms of ordinary dictionary significance are used.

Botanical classification: *Pelargonium grandiflorum* cultivar Regburg.

Parentage:

*Female, or seed, parent.*—Unnamed proprietary selection of *Pelargonium grandiflorum*, not patented.

*Male or pollen parent.*—Unnamed proprietary selection of *Pelargonium grandiflorum*, not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer.*—About 25 days at temperatures of 20° C.

*Time to produce a rooted young plant, winter.*—About 30 days at temperatures of 20° C.

*Root description.*—Fine, fibrous; white in color.

*Rooting habit.*—Freely branching; dense.

Plant description:

*Plant/growth habit.*—Upright and mounded plant habit; inverted triangle; densely foliated. Vigorous growth habit. Freely basal branching habit with about seven lateral branches developing per plant.

*Plant height, to top of umbels.*—About 28 cm.

*Plant height, to top of leaves.*—About 16 cm.

*Plant width.*—About 35 cm.

*Lateral branches.*—Length: About 10 cm. Diameter: About 8 mm. Internode length: About 1 cm to 2 cm. Texture: Pubescent. Color: 144A.

Foliage description:

*Arrangement.*—Alternate or opposite; simple.

*Length.*—About 7 cm.

*Width.*—About 9 cm.

*Shape.*—Roughly cordate; palmately lobed.

*Apex.*—Acute.

*Base.*—Cordate, open.

*Margin.*—Serrate to biserrate.

*Venation pattern.*—Palmate.

*Texture, upper surface.*—Smooth, glabrous; leathery.

*Texture, lower surface.*—Slightly pubescent on veins; leathery.

*Color.*—Developing and fully expanded foliage, upper surface: 137B; venation, 137B. Developing and fully expanded foliage, lower surface: 147B; venation, 144A. Zonation pattern: Not discernible. Petiole: Length: About 6 cm. Diameter: About 4 mm. Texture, upper and lower surfaces: Pubescent. Color, upper and lower surfaces: 144A.

Flower description:

*Flower arrangement.*—Single rotate flowers arranged in inversely conical umbels arising from apical leaf axils. Umbels displayed above the foliage on strong peduncles. Flowers face upright to outward. Flowers not persistent. Flowers not fragrant.

*Quantity of flowers.*—Freely flowering habit; about 25 flower umbels per plant each with about four to six flowers.

*Flowering season.*—In Dresden, Germany, flowering initiates in the spring and continues into the summer. Plants do not require a cooling treatment for flower development.

*Flower longevity.*—Individual flowers last about two weeks on the plant.

*Umbel height.*—About 7 cm.

*Umbel diameter.*—About 9 cm.

*Flower diameter.*—About 6 cm.

*Flower depth (height).*—About 3 cm.

*Flower buds.*—Length: About 1.5 cm. Diameter: About 7 mm. Shape: Roughly elliptical. Color: 146B.

*Petals.*—Quantity per flower: Five; imbricate. Length: About 4 cm. Width: Upper two petals, about 2.8 cm. Lower three petals, about 1.9 cm. Shape: Obovate. Apex: Rounded. Base: Cuneate. Margin: Entire. Texture, upper and lower surfaces: Smooth, glabrous; satiny. Color: When opening, upper surface: More violet in color than 61A; center, darker than 187A. When opening, lower surface: 78B. Fully opened, upper surface, upper two petals: 74A; center, darker than 187A; towards the base, 59A; venation, darker than 59A. Fully opened, upper surface, lower three petals: 61A; small central spot, darker than 187A; towards the base, 59A; venation, darker than 59A. Fully opened, lower surface: 78B; towards the base, close to 155D; venation, darker than 59A.

*Sepals.*—Quantity per flower: Five, arranged in a single whorl. Length: About 1.7 cm. Width: About 5 mm. Shape: Lanceolate. Apex: Acute. Margin: Entire. Texture, upper and lower surfaces: Pubescent. Color, upper and lower surfaces: 146B.

*Peduncle (umbel stem).*—Length: About 5 cm. Diameter: About 2 mm. Strength: Strong. Angle: Mostly erect to outwardly slanted. Texture: Pubescent. Color: 146B.

*Pedicel (individual flower stem).*—Length: About 3 cm. Diameter: About 1 mm. Strength: Strong; flexible. Texture: Pubescent. Color: 146B.

*Reproductive organs.*—Androecium: Stamen quantity per flower: About seven. Anther length: About 2 mm. Anther shape: Tubular. Anther color: 72A. Pollen amount: Abundant. Pollen color: 171A. Gynoecium: Pistil quantity per flower: One. Pistil length: About 2 cm. Stigma shape: Five-parted. Stigma color: Darker than 59A. Style length: About 4 mm. Style color: Darker than 59A. Ovary color: Close to 146C.

*Seeds.*—Length: About 2 mm to 3 mm. Diameter: About 1 mm. Color: Brownish.

Disease/pest resistance: Plants of the new Regal *Geranium* have not been observed to be resistant to pathogens and pests common to Regal *Geraniums*.

Temperature tolerance: Plants of the new Regal *Geranium* have been observed to tolerate temperatures ranging from about 1° C. to about 35° C. to 40° C.

It is claimed:

1. A new and distinct Regal *Geranium* plant named 'Regburg' as illustrated and described.

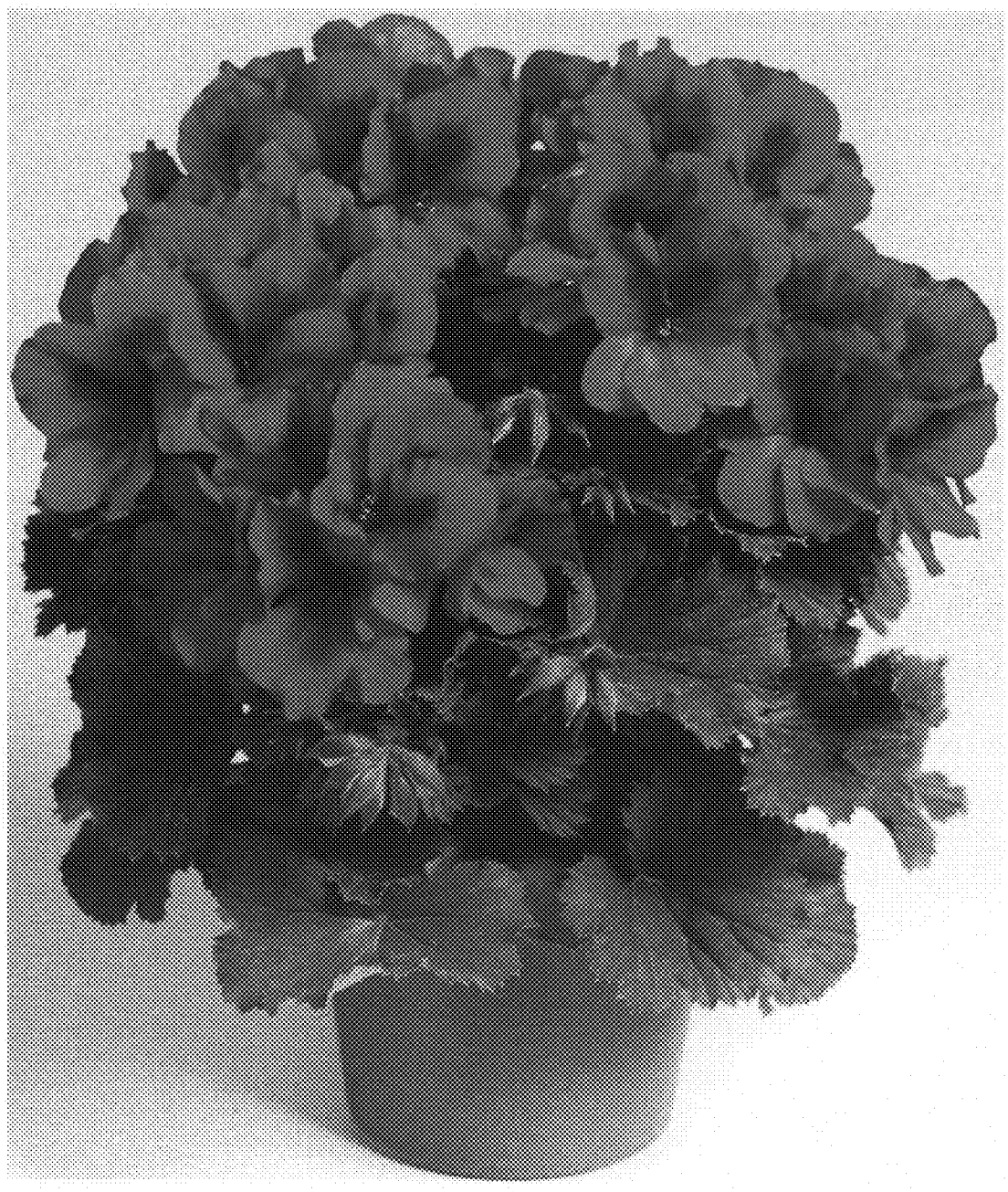

* * * * *